(12) United States Patent
Naik et al.

(10) Patent No.: US 9,073,901 B2
(45) Date of Patent: Jul. 7, 2015

(54) DGAT2 INHIBITORS

(71) Applicant: Eli Lilly and Company, Indianapolis, IN (US)

(72) Inventors: Manisha Naik, Reading (GB); Nicholas Paul Camp, Surrey (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/547,615

(22) Filed: Nov. 19, 2014

(65) Prior Publication Data

US 2015/0148358 A1 May 28, 2015

Related U.S. Application Data

(60) Provisional application No. 61/908,339, filed on Nov. 25, 2013.

(51) Int. Cl.
*A01N 43/54* (2006.01)
*A61K 31/505* (2006.01)
*C07D 403/12* (2006.01)

(52) U.S. Cl.
CPC .................................. *C07D 403/12* (2013.01)

(58) Field of Classification Search
None
See application file for complete search history.

(56) References Cited

U.S. PATENT DOCUMENTS

| | | | |
|---|---|---|---|
| 7,732,590 B2 | 6/2010 | Bhanot et al. | |
| 7,825,235 B2 | 11/2010 | Bhanot et al. | |
| 7,910,346 B2 | 3/2011 | Gimeno et al. | |
| 8,258,289 B2 | 9/2012 | Bhanot et al. | |
| 2005/0288213 A1 | 12/2005 | MacNeil et al. | |
| 2008/0200376 A1 | 8/2008 | MacCoss et al. | |
| 2011/0237505 A1 | 9/2011 | Burow et al. | |

FOREIGN PATENT DOCUMENTS

| | | |
|---|---|---|
| WO | 2008129080 A1 | 10/2008 |
| WO | 2011116951 A1 | 9/2011 |
| WO | 2013026874 A1 | 2/2013 |
| WO | 2013026890 A1 | 2/2013 |
| WO | 2013150416 A1 | 10/2013 |

OTHER PUBLICATIONS

Cases, S., et al, Cloning of DGAT2, a Second Mammalian Diacylglycerol Acyltransferase, and Related Family Members, J. Biol. Chem., 2001, pp. 38870-38876, vol. 276, No. 42.
Chan, D.C., et al, Postprandial Hypertriglyceridemia and Cardiovascular Disease: Current and Future Therapies, Cirr. Atherosclear Rep., 2013, pp. 1-9, vol. 15, No. 309.
Cheng, D., et al, Human Acyl-CoA: Diacylglycerol Acyltransferase is a Tetrameric Protein, Biochem. J., 2001, pp. 707-714, 359.
Choi, C.S., et al, Supression of Diacylglycerol Acyltransferase-2 (DGAT2), but Not DGAT1, with Antisense Oligonucleotides Reverses Diet-induced Hepatic Steatosis and Insulin Resistance, J. Biol. Chem., Aug. 3, 2007, pp. 22678-22688, vol. 282, No. 31.
Dow, R.L., et al, Design and Synthesis of Potent, Orally-Active DGAT-1 Inhibitors Containing a Dioxino[2,3-d] pyrimidine Core, Bioorg. & Med. Chem. Letters, 2011, pp. 6122-6125, vol. 21, No. 20.
Kim, M.O., Identification and Validation of a Selective Small Molecule Inhibitor Targeting the Diacylglycerol Acyltransferase 2 Activity, Biol. Pharm. Bull., Jul. 2013, pp. 1167-1173, vol. 36, No. 7.
Devita, R.J., Current Status of the Research and Development of Diacylglycerol O-Acyltransferase 1 (DGAT1) Inhibitors, J. Med. Chem., May 10, 2013, pp. 9820-9825, vol. 56.
Lee, K., Discovery of Indolyl Acrylamide Derivatives as Human Diacylglycerol Acyltransferase-2 Selective Inhibitors, Org. Biomol. Chem., 2013, pp. 849-858, vol. 11.
Liu, Y., Knockdown of Acyl-CoA:diacylglycerol Acyltransferase 2 with Antisense Oligonucleotide Reduces VLDL TG and ApoB Secretion in Mice, Biochimica et Biophysica Acta, 2008, pp. 97-104, vol. 1781.
Miller, M. et al, Triglycerides and Cardiovascular Disease a Statement from the American Heart Association, Circulation, 2011, pp. 2292-2333, vol. 123.
Qi, J., et al, The Use of Stable Isotope-labeled Glycerol and Oleic Acid to Differentiate the Hepatic Functions of DGAT1 and -2, J. of Lipid Research, 2012, pp. 1106-1116, vol. 53.
Tep, S., Rescue of Mtp siRNA-induced Hepatic Steatosis by DGAT2 siRNA Silenceing, J. of Lipid Research, 2012, pp. 859-867, and 2484, vol. 53.
Wurie, H.R., Diacylglycerol Acyltransferase 2 Acts Upstream of Diacylglycerol Acyltransferase 1 and Utilizes Nascent Diglycerides and de novo Synthesized Fatty Acids in HepG2 Cells, FEBS Journal, 2012, pp. 3033-3047, vol. 279.

*Primary Examiner* — Craig Ricci
*Assistant Examiner* — Jared D Barsky
(74) *Attorney, Agent, or Firm* — James B. Myers

(57) ABSTRACT

The present invention provides compounds of the Formula below:

where R is H or —CH$_3$; methods of treating patients for hypertriglyceridemia and cardiovascular disease including dyslipidemia and atherosclerosis, and processes for preparing the compounds.

15 Claims, No Drawings

DGAT2 INHIBITORS

The present invention is directed to novel compounds useful for inhibiting Diacylglycerol O-acyltransferse 2 (DGAT2), which may provide useful therapies for treating elevated triglyceride levels and cardiovascular diseases including dyslipidemia and atherosclerosis. The present invention is also directed to a process for preparing the novel compounds.

The average triglyceride level in people, particular in populations in the western hemisphere, has risen at an alarming rate in the last 30 years. The increase in triglyceride levels, or hypercholesterolemia, has been associated with a number of disease risks including an increased risk of cardiovascular diseases such as dyslipidemia and atherosclerosis. The increase in triglyceride levels has also coincided with a dramatic increase in obesity, insulin resistance, type-2-diabetes, hepatic steatosis and non-alcoholic fatty liver disease (NAFLD). Because elevated triglyceride levels are implicated in a variety of diseases and conditions, controlling the either the production and/or level of triglyceride levels may provide a viable treatment for metabolic disease.

Diacylglycerol O-acyltransferse 2 (DGAT2) is expressed in many tissues; however, it is expressed mainly in the liver and white adipose tissue. It is implicated, along with DGAT1, in the last step for triglyceride synthesis. The inhibition of DGAT2 activity leading to a reduction in triglyceride levels will suppress low density lipoprotein cholesterol (LDL-c) by controlling either production via ApoB secretion or deposition of those particles. Both mechanisms are pharmacologically validated in humans. Limiting secretion of apolipoprotein B (ApoB) particles reduces LDL-c production. Therefore attenuation of DGAT2 activity has favorable impact on triglyceride levels, LDL-c, ApoB, and triglyceride-rich lipoprotein concentration in circulation and lipogenesis in the liver.

WO2013/150416 discloses certain derivatives of purine, pyrimidine, and pyrazine compounds as DGAT2 inhibitors and their use in treating diseases associated to DGAT2 activity.

There is a need for additional drugs for the treatments for hypercholesterolemia and cardiovascular diseases such as dyslipidemia and athrosclerosis. Current treatment methods, which include diet, lifestyle changes, and/or statin therapy may not lower LDL-c levels sufficiently for all patients at risk for cardiovascular diseases. Further there is a subset of patients that are intolerant or become intolerant to statin therapy. The present invention addresses one or more of these needs by providing alternative compounds and treatment methods, which may be suitable for the treatment cardiovascular diseases.

The present invention provides a compound according to Formula I

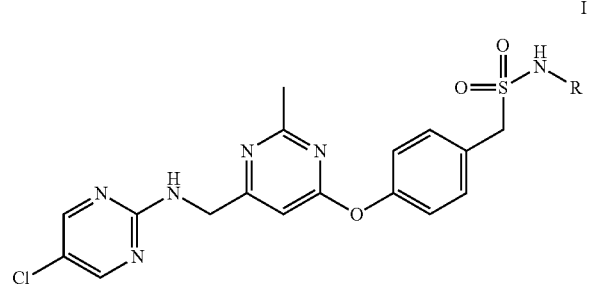

Where R is H or —$CH_3$ or a pharmaceutically acceptable salt thereof.

In one form, the present invention provides a compound of Formula I wherein R is H or a pharmaceutically acceptable salt thereof.

In another form, the present invention provides a compound of Formula I wherein R is —$CH_3$ or a pharmaceutically acceptable salt thereof.

The present invention provides a method for treating a patient in need of treatment for cardiovascular disease. The method comprises administering to the patient a compound according to Formula I, or a pharmaceutically acceptable salt thereof. In one embodiment the administered compound, or pharmaceutically acceptable salt thereof, is a compound of Formula I wherein R is H. In another embodiment the administered compound, or pharmaceutically salt thereof, is a compound of Formula I wherein R is —$CH_3$.

In another form, the present invention provides a method for treating a patient in need of treatment for dyslipidemia. The method comprises administering to the patient a compound of the present invention according to Formula I, or a pharmaceutically acceptable salt thereof. In one embodiment the administered compound, or pharmaceutically acceptable salt thereof, is a compound of Formula I wherein R is H. In another embodiment the administered compound or pharmaceutically salt thereof is a compound of Formula I wherein R is —$CH_3$.

In yet another form, the present invention provides a method for treating a patient in need of treatment for atherosclerosis. The method comprises administering to the patient a compound according to Formula I, or a pharmaceutically acceptable salt thereof. In one embodiment the administered compound, or pharmaceutically acceptable salt thereof, is a compound of Formula I wherein R is H. In another embodiment the administered compound, or pharmaceutically salt thereof, is a compound of Formula I wherein R is —$CH_3$.

In one form, the present invention provides a method for treating a patient in need of treatment for hypertriglyceridemia. The method comprises administering to the patient a compound according to Formula I, or a pharmaceutically acceptable salt thereof. In one embodiment the administered compound, or pharmaceutically acceptable salt thereof, is a compound of Formula I wherein R is H. In another embodiment the administered compound, or pharmaceutically salt thereof, is a compound of Formula 1 wherein R is —$CH_3$.

The present invention provides a pharmaceutical composition comprising a compound of Formula I, or a pharmaceutically acceptable salt thereof, and at least one of a pharmaceutically acceptable carrier or excipient. In one embodiment, present invention provides a compound of Formula I wherein R is H, or a pharmaceutically acceptable salt thereof. In another embodiment the present invention includes a compound of Formula I wherein R is —$CH_3$, or a pharmaceutically acceptable salt thereof.

Such pharmaceutical compositions and processes for preparing the compositions are known in the art. (See e.g., Remington; The Science and Practice of Pharmacy, D. B. Troy, Editor, 21$^{st}$ Edition, Lippinncott, Williams & Wilkins, 2006).

The present invention provides a method for treating a patient in need of treatment for cardiovascular disease, dyslipidemia, atherosclerosis, or hypertriglyceridemia. The method comprises administering to the patient a pharmaceutical composition comprising a compound according to Formula I, or a pharmaceutically acceptable salt thereof. In one embodiment the administered pharmaceutical composition comprises of Formula I wherein R is H or pharmaceutically acceptable salt thereof. In another embodiment the administered compound or pharmaceutical composition comprises a compound of Formula I wherein R is —$CH_3$, or pharmaceutically acceptable salt thereof.

The present invention provides a compound of the invention for use in therapy. In one embodiment the compound or pharmaceutically acceptable salt thereof is a compound of Formula I wherein R is H. In another embodiment the compound or pharmaceutically salt thereof is a compound of Formula I wherein R is —$CH_3$.

In one embodiment the therapy comprises the use of a compound of the invention for the treatment of cardiovascular disease. The compound or pharmaceutically acceptable salt thereof is a compound of Formula I wherein R is H. Alternatively, the compound or pharmaceutically salt thereof is a compound of Formula I wherein R is —$CH_3$.

In one embodiment the therapy comprises the use of a compound of the invention for the treatment of dyslipidemia. The compound or pharmaceutically acceptable salt thereof is a compound of Formula I wherein R is H. Alternatively, the compound or pharmaceutically salt thereof is a compound of Formula I wherein R is —$CH_3$.

In another embodiment, the therapy comprises the use of a compound of the invention for the treatment of atherosclerosis. The compound or pharmaceutically acceptable salt thereof is a compound of Formula I wherein R is H. Alternatively, the compound or pharmaceutically salt thereof is a compound of Formula I wherein R is —$CH_3$.

In another embodiment, the therapy comprises the use of a compound of the invention for the treatment of hypertriglyceridemia. The compound or pharmaceutically acceptable salt thereof is a compound of Formula I wherein R is H. Alternatively, the compound or pharmaceutically salt thereof is a compound of Formula I wherein R is —$CH_3$.

The present invention also includes the use of a compound according to Formula I in the manufacture of a medicament to treat one or more of: hypertriglyceridemia, cardiovascular disease, dyslipidemia, and atherosclerosis. In one embodiment the compound or pharmaceutically acceptable salt thereof is a compound of Formula I wherein R is H. In another embodiment the compound or pharmaceutically salt thereof is a compound of Formula I wherein R is —$CH_3$.

The present invention provides a process for the preparation of a compound of Formula 2 below:

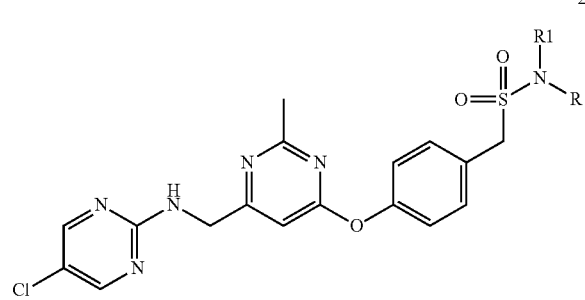

wherein R is H or —$CH_3$ and R1 is a protecting group. The method comprises reacting a compound of Formula 3

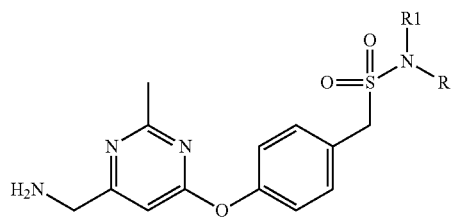

with a compound of Formula 4 below:

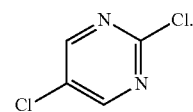

The preparation can further comprise the step of removing the protecting group, R1, of Formula 2 to provide the compound of Formula I.

Examples of various amino protecting functionalities include: carbamates such as $C_{1-5}$ alkyl carbamate, $C_{3-6}$ cycloalkyl carbamate, preferably a t-butyl carbamate, (BOC) or benzyl carbamate (CBZ); amides such as $C_{1-3}$ alkylamide $C_{1-3}$ haloalkylamide, formamide or acetamide chloroacetamide, trifluoridoacetamide; and benzyl amines. Further examples of amino protecting functionalities, methods of preparing the protected amino substituents, and methods for deprotecting the amino substituents can be found in "Protecting Groups in Organic Synthesis", 3rd Ed. Greene, T. W., Wuts, P. G. M., Eds., John Wiley and Sons, New York, 1999. It will be recognized by those skilled in the art that in addition to the protected amino substituent other functional groups that can be readily converted to the amino group can be used. Such functional groups, preparations, and transformations of these groups can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

The term "pharmaceutically-acceptable salt" as used herein refers a salt of a compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

As used herein, the term "effective amount" of a compound of Formula I refers to an amount, that is a dosage, which is effective in treating a disorder, such as cardiovascular disease, dyslipidemia, atherosclerosis, or hypertriglyceridemia. The attending diagnostician, as one skilled in the art, can readily determine an effective amount by the use of conventional techniques and by observing results obtained under analogous circumstances. In determining an effective amount or dose of a compound of Formula I, a number of factors are considered, including, but not limited to which of the compounds of Formula I will be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

As used herein, the terms "treating", "to treat", or "treatment", includes restraining, slowing, stopping, reducing, or reversing the progression or severity of an existing symptom, disorder, condition, or disease.

As used herein, the term "patient" refers to a mammal, preferably a human or companion mammal such as a dog or cat.

General Chemistry

As used herein, the following terms have the meanings indicated: "DCM" refers to dichloromethane; "Et$_2$O" refers to diethylether; "DMF" refers to dimethylformamide; "DMSO" refers to dimethylsulfoxide; "EtOAc" refers to ethyl acetate "EtOH" refers to ethanol; "hr" refers to hour; "m" refers to minutes; "MeOH' refers to methanol; "MS" refers to mass spectroscopy; "RT" refers to room temperature; "THF" refers to tetrahydrofuran.

Unless noted to the contrary, the compounds illustrated herein are named and numbered using Accelrys Draw 4.0.

Scheme 1 illustrates a general synthesis of compounds of Formula I and 2.

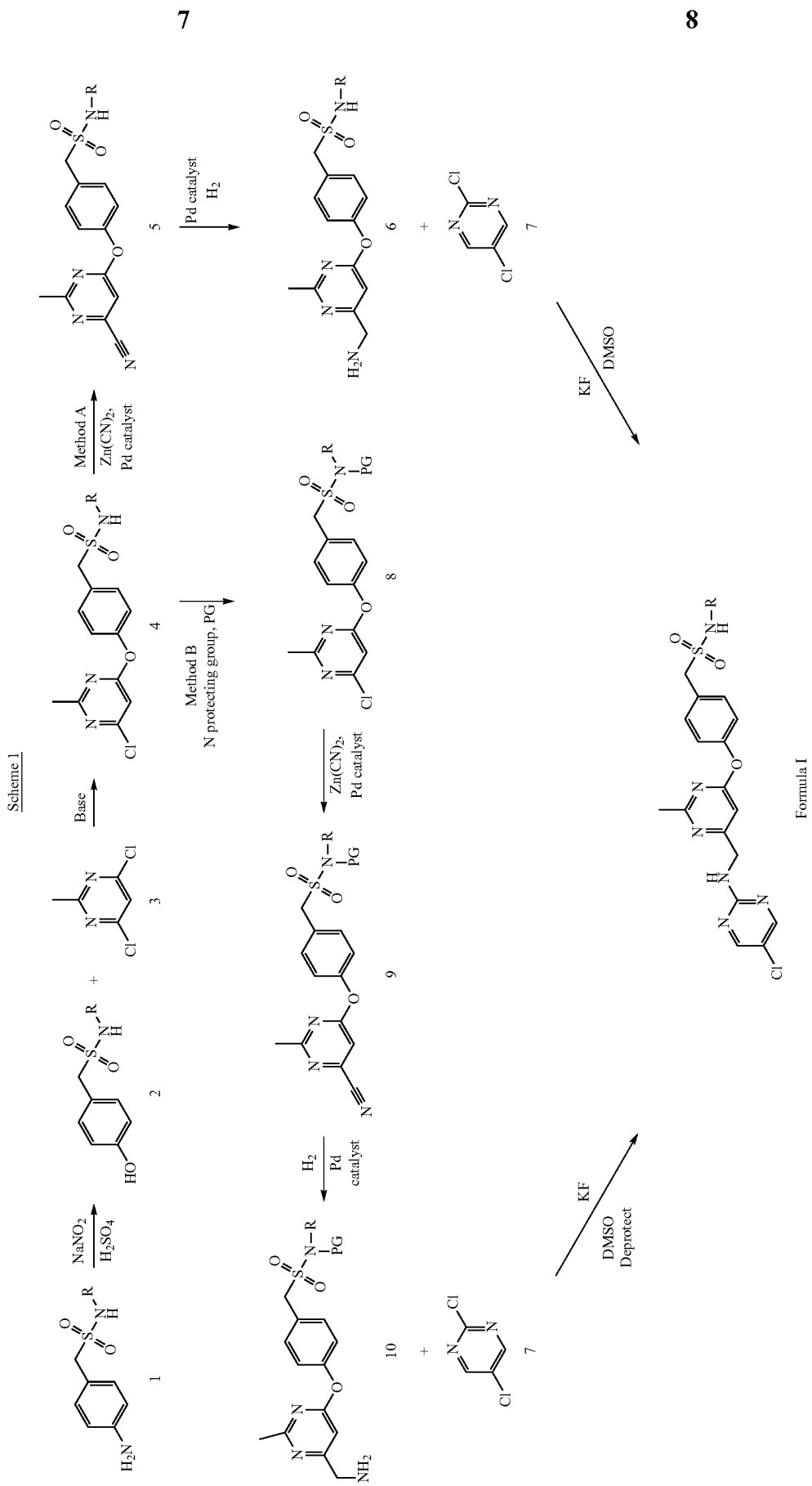

In general, the sulfonamide, compound 1, can be converted to the phenol derivative, compound 2, using sodium nitrite and sulfuric acid. Reaction of compound 2 with 4,6-dichloro-2-methylpyrimidine, compound 3, provides the ether compound 4.

Following Method A, the chloride substituent of compound 4 can be converted to the cyano group, for compound 5, using zinc cyanide and a palladium catalyst. The cyano group on compound 5 can be reduced to the amino group on compound 6 using a palladium catalyst and hydrogen gas. Reaction of the amine compound 6 with 2,5-dichloropyrimidine, compound 7, provides compounds of Formula I, where R can be either H or a methyl group.

Alternatively according to Method B, the sulfonamide nitrogen of compound 4, can be protected with known nitrogen protecting groups to provide compound 8. The chloride substituent of compound 8 can be converted to the cyano group, on compound 9, using zinc cyanide and a palladium catalyst. The cyano group on compound 9 can be reduced to the amino group on compound 10 using a palladium catalyst and hydrogen gas. Reaction of the amine compound 10 with 2,5-dichloropyrimidine, compound 7 and concomitant (or subsequent) de-protection of the nitrogen provides compounds of Formula I, where R can be H or a methyl group.

EXAMPLE 1

1-[4-[6-[[(5-Chloropyrimidin-2-yl)amino]methyl]-2-methyl-pyrimidin-4-yl]oxyphenyl]-N-methyl-methanesulfonamide

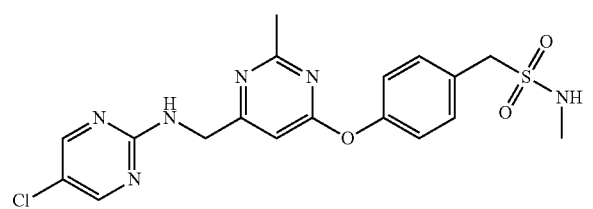 [SMILES: CNS(=O)(=O)Cc1ccc(Oc2cc(CNc3ncc(Cl)cn3)nc(C)n2)cc1]

The compound of Example 1 can be made by either Method A or Method B as set forth below.

Method A

Preparation 1

1-(4-Hydroxyphenyl)-N-methyl-methanesulfonamide

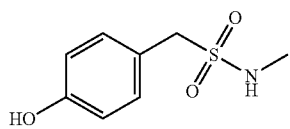

Add sulfuric acid (2.5 mL, 44.9 mmol) to a suspension of 1-(4-aminophenyl)-N-methyl-methanesulfonamide (7.5 g, 37.5 mmol) in water (56.2 mL) and chill the reaction mixture to 0° C. Slowly, drop wise add a solution of sodium nitrite (2.8 g; 41.2 mmol) in water (37.5 mL) to this slurry. Stir the resulting mixture at 0° C. for 20 m, then remove the ice bath and heat the reaction at 100° C. Cool the mixture to room temperature. Quench the reaction with an excess of water and extract with EtOAc. Combine the EtOAc extracts, wash the extracts with brine; dry over $MgSO_4$; filter; and concentrate the filtrate under reduced pressure to yield the title compound as an orange solid (6.2 g, 66%). MS (m/z): 219 (M+$H_2O$).

Preparation 2

1-[4-(6-Chloro-2-methyl-pyrimidin-4-yl)oxyphenyl]-N-methyl-methanesulfonamide

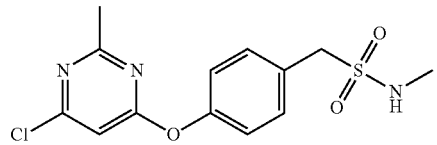 [SMILES: CNS(=O)(=O)Cc1ccc(Oc2cc(Cl)nc(C)n2)cc1]

Under nitrogen atmosphere add potassium carbonate (26.4 g, 190.8 mmol) to a solution of 1-(4-hydroxyphenyl)-N-methyl-methanesulfonamide (19.2 g, 95.4 mmol), and 4,6-dichloro-2-methylpyrimidine (15.6 g, 95.4 mmol) in DMSO (192.0 mL). Stir the resulting mixture at room temperature for 2 hours. Pour the mixture into 400 mL of ice/water (1:1 v/v) to induce precipitation. Stir the resulting suspension for 30 minutes. Collect the solid; wash with water; and dry under reduced pressure overnight to provide the title compound as a pale brown solid (27.7 g, 89%). MS (m/z): 328 (M+1).

Preparation 3

1-[4-(6-Cyano-2-methyl-pyrimidin-4-yl)oxyphenyl]-N-methyl-methanesulfonamide

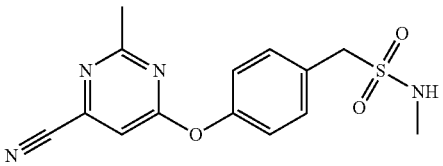 [SMILES: CNS(=O)(=O)Cc1ccc(Oc2cc(C#N)nc(C)n2)cc1]

Bubble nitrogen gas through a solution of 1-[4-(6-chloro-2-methyl-pyrimidin-4-yl)oxyphenyl]-N-methyl-methanesulfonamide (26.6, 81.1 mmol) in DMF (266.0 mL) for 15 minutes. Thereafter add zinc cyanide (14.59 g, 121.2 mmol) and (1,1'-bis(diphenylphosphino)ferrocene)palladium(II) chloride (6.76 g, 8.1 mmol). Heat the suspension to 150° C. for 6 hr while maintaining it under a nitrogen atmosphere. Cool the mixture to room temperature. Dilute the mixture with water (600 mL) and extract the mixture with EtOAc (3×500 mL). Combine the EtOAc extracts. Sequentially wash the combined extracts with water (500 mL) then brine (500 mL); dry over sodium sulfate; filter and concentrate the filtrate under reduced pressure. Isolate the title compound using silica gel chromatography eluting with hexane/EtOAc (1:1) to give the title compound (18 g, 70%). MS (m/z): 319 (M+1).

Alternative Preparation 3

Add, portion-wise, potassium carbonate (325 mesh, 46.5 g, 329.9 mmoles) to a mixture of 1-(4-hydroxyphenyl)-N-methyl-methanesulfonamide (40.0 g, 165.0 mmoles) and 6-chloro-2-methyl-pyrimidine-4-carbonitrile (26.6 g, 173.2 mmoles) in acetone (400.0 mL). Stir the mixture for 3 h at 22°

C. Filter the resulting suspension and rinse the solid with acetone. Combine the filtrate and washing, (discard the solid). Concentrate filtrate to provide a brown solid. Slurry the solid in methyl tert-butyl ether (120 mL) and filter. Collect the solid and slurry it with methyl tert-butyl ether (80 mL) and then filter. Rinse the solid with methyl tert-butyl ether (80 mL) to give light brown solid. Dry in a vacuum oven, 40° C., 50 mbar for 8 h to provide title compound as light brown solid, 52.4 g, 97% yield. MS (m/z): 319 (M+1).

Preparation 4

1-[4-[6-(Aminomethyl)-2-methyl-pyrimidin-4-yl] oxyphenyl]-N-methyl-methanesulfonamide

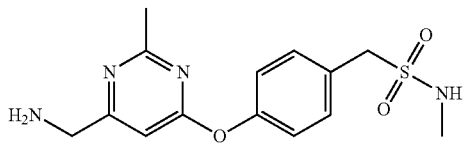 [SMILES: CNS(=O)(=O)Cc1ccc(Oc2cc(CN)nc(C)n2)cc1]

In a PARR reactor, combine palladium (3.6 g, 10% on charcoal, 1-[4-(6-cyano-2-methyl-pyrimidin-4-yl)oxyphenyl]-N-methyl-methanesulfonamide (18 g, 56.5 mmol), EtOH (270 mL), EtOAc (270 mL), and triethylamine (31.5 mL). Seal the PARR reactor and charge it with hydrogen (400 psi); then shake the reactor at room temperature overnight. Open the reactor and filter the contents through CELITE®; wash the CELITE® pad with EtOH (1000 mL); collect the filtrate; and evaporate the solvent to provide the title compound as a brown solid (11.1 g, 43%). MS (m/z): 323 (M+1).
Alternative Preparation 4

Combine palladium (18.54 g, 10% on charcoal), 1-[4-(6-cyano-2-methyl-pyrimidin-4-yl)oxyphenyl]-N-methyl-methanesulfonamide (46.34 g, 141.19 mmol), 1,4-Dioxane (278 mL), EtOH (185 mL), and triethylamine (78.7 mL) in a PARR reactor. Seal the PARR reactor and charge it with hydrogen (400 psi). Shake the reactor at room temperature for 4.5 h. Open the reactor and filter the contents through CELITE®. Collect and evaporate the filtrate to provide the title compound as a yellow solid (23.8 g, 48%). MS (m/z): 323 (M+1). Wash the CELITE® pad with a mixture of 1,4-dioxane/MeOH (6×500 mL); collect the filtrate; and evaporate the solvent to provide a second crop of the title compound as a yellow solid (pinky solid, 48%). MS (m/z): 323 (M+1).

EXAMPLE 1

1-[4-[6-[[(5-Chloropyrimidin-2-yl)amino]methyl]-2-methyl-pyrimidin-4-yl]oxyphenyl]-N-methyl-methanesulfonamide

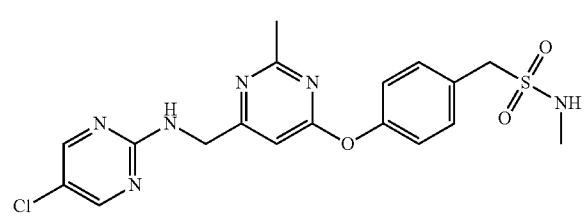 [SMILES: CNS(=O)(=O)Cc1ccc(Oc2cc(CNc3ncc(Cl)cn3)nc(C)n2)cc1]

Add potassium fluoride (1.82 g, 31.33 mmol) to a solution of 1-[4-[6-(aminomethyl)-2-methyl-pyrimidin-4-yl]oxyphenyl]-N-methyl-methanesulfonamide (11.1 g, 24.10 mmol) and 2,5-dichloropyrimidine (4.31 g, 28.92 mmol) in DMSO (111 mL). Heat the reaction mixture at 120° C. for two hours. Thereafter cool the mixture to room temperature; add water (200 mL), and extract with EtOAc (3×200 mL). Combine the organic extracts; sequentially wash the organic extracts with water (300 mL) then brine (300 mL); dry over sodium sulfate; filter; and concentrate the filtrate under reduced pressure to provide title compound as a crude material. Purify the title compound using silica gel chromatography eluting with a gradient of hexane/EtOAc (1:1) to EtOAc (100%). Collect the relevant fractions containing the title compound and concentrate the fractions. Dissolve the resulting material in THF (200 mL) and EtOAc (300 mL), then add SiliaMetS® Thiol (9.2 g) to remove traces of palladium. Stir the mixture for 2 hr at 55° C. Filter the mixture at 55° C.; collect the filtrate; and evaporate the solvent to provide a solid. Triturate the solid with cold EtOAc (20 mL); collect the solid by filtration; and dry the solid under reduced pressure to provide the title compound as a white solid (8 g, 75%). MS (m/z): 435 (M+1).

ALTERNATIVE PREPARATION FOR EXAMPLE 1

Combine 1-[4-[6-(aminomethyl)-2-methyl-pyrimidin-4-yl]oxyphenyl]-N-methyl-methanesulfonamide (23.6 g, 67.3 mmol) and 2,5-dichloropyrimidine (10.03 g, 67.3 mmol) in DMSO (236 mL). Stir the mixture at 22° C. for 1 h. Add potassium fluoride (5.14 g, 87.5 mmol). Heat the reaction mixture to 120° C. for two hours. Thereafter cool the mixture to room temperature and pour it into water/ice (250 mL). Add additional water (50 mL) and place the mixture in ultrasound bath for 30 min Collect the resulting solid material. Slurry the solid with water (100 mL) and collect the solid to provide the title compound as yellow solid, 25.7 g, 82% yield. MS (m/z): 435 (M+1).

Purify the compound by flash chromatography (1500 g SiO$_2$ column; eluent: hexane/EtOAc 50:50 to 25:75; 1 L fractions, charge in DCM/MeOH 30:1, 600 mL). Collect and concentrate appropriate fractions. Dry the resulting solid in vacuum oven, 45° C., 5 mbar for 18 h to give title compound as white solid, MS (m/z): 435 (M+1).

Method B

Preparation 5 tert-Butyl N-[[4-(6-chloro-2-methyl-pyrimidin-4-y) oxyphenyl]methylsulfonyl]-N-methyl-carbamate

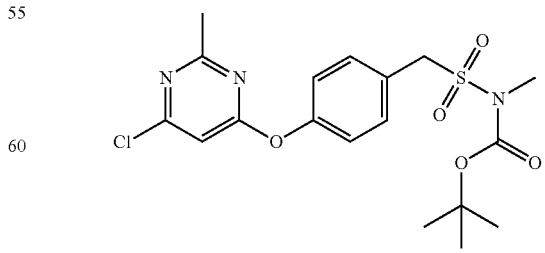

Dissolve 1-[4-(6-chloro-2-methyl-pyrimidin-4-y)oxyphenyl]-N-methyl-methanesulfonamide (2.41 g, 4.6 mmol) (See Preparation 2) in DCM (10 mL) and add N,N-dimethyl-4-pyridinamine (56.6 mg, 0.46 mmol). Cool the solution to 0° C.; add tert-butoxycarbonyl tert-butyl carbonate (1.5 g, 6.8 mmol); and stir for one hour. Quench the reaction with an excess of 0.5 N HCl. Extract the mixture with DCM. Combine the DCM extracts; wash the extracts with brine; dry over magnesium sulfate; filter and concentrate the filtrate under reduced pressure to provide the title compound as an orange oil (3.03 g, 99.4%). MS (m/z): 428 (M+1).

Preparation 6 tert-Butyl N-[[4-(6-cyano-2-methyl-pyrimidin-4-y)oxyphenyl]methylsulfonyl]-N-methyl-carbamate

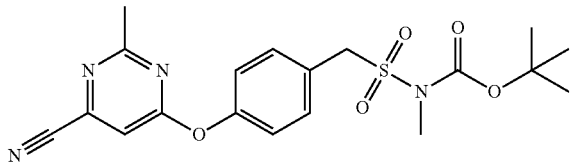 [SMILES: Cc1nc(C#N)cc(Oc2ccc(CS(=O)(=O)N(C)C(=O)OC(C)(C)C)cc2)n1]

Under an atmosphere of nitrogen, combine tert-butyl N-[[4-(6-chloro-2-methyl-pyrimidin-4-y)oxyphenyl]methylsulfonyl]-N-methyl-carbamate (2.24 g, 3.4 mmol), DMF (2 mL), tetrakis(triphenylphosphine)palladium (1.9 g, 1.7 mmol), and zinc cyanide (2.0 g, 16.8 mmol). Heat the mixture to 90° C. and stir for 3 hours. Quench the reaction with water and sodium hydroxide. Extract the mixture with EtOAc; wash the EtOAc extract(s) with brine; dry over magnesium sulfate; filter and concentrate the filtrate under reduced pressure to provide a residue. Purify the title compound via flash column chromatography using 80 g of silica gel, and eluting with a 0-55% gradient of EtOAc in hexanes. Evaporate the relevant fractions to provide the title compound as a yellow oil (1.2 g, 80.9%). MS (m/z): 419 (M+1).

Preparation 7 tert-Butyl N-[[4-[6-(aminomethyl)-2-methyl-pyrimidin-4-yl]oxyphenyl]methylsulfonyl]-N-methyl-carbamate

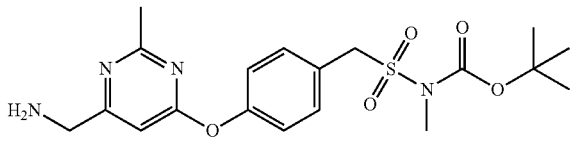 [SMILES: Cc1nc(CN)cc(Oc2ccc(CS(=O)(=O)N(C)C(=O)OC(C)(C)C)cc2)n1]

Combine tert-butyl N-[[4-(6-cyano-2-methyl-pyrimidin-4-y)oxyphenyl]methylsulfonyl]-N-methyl-carbamate (400 mg, 0.96 mmol), triethylamine (290 mg, 2.9 mmol), MeOH (20 mL), and EtOAc (20 mL) in a PARR reactor. Add 5% palladium on carbon (203 mg, 0.096 mmol). Seal the PARR reactor and pressurize it with hydrogen (345 kPa). Shake the reactor at ambient temperature for 17 hours. Depressurize and open the reactor. Add an additional amount of 5% palladium on carbon (200 mg, 0.094 mmol); re-pressurize the reactor with hydrogen (414 kPa) and shake the reactor for an addition 17 hours while maintaining it at ambient temperature. Depressurize and open the reactor. Filter the contents through diatomaceous earth, and concentrate the filtrate under reduced pressure to provide a residue. To purify, add toluene and concentrate under reduced pressure to provide an orange-red residue. Repeat the toluene addition and removal 3 times to provide the title compound as a pink solid (0.57 g, 98.8%, 70% pure). MS (m/z): 423 (M+1).

EXAMPLE 1

1-[4-[6-[[(5-Chloropyrimidin-2-yl)amino]methyl]-2-methyl-pyrimidin-4-yl]oxyphenyl]-N-methyl-methanesulfonamide

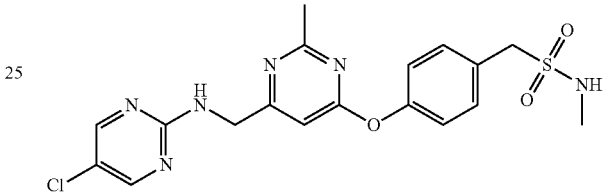

Add potassium fluoride (53.9 mg, 0.93 mmol) to a solution of tert-butyl N-[[4-[6-(aminomethyl)-2-methyl-pyrimidin-4-yl]oxyphenyl]methylsulfonyl]-N-methyl-carbamate (280 mg, 0.46 mmol) and 2,5-dichloropyrimidine (69.1 mg, 0.46 mmol) in DMSO (10 mL). Heat the mixture to 120° C. and stir it at that temperature for 17 hours. Cool the mixture to ambient temperature and quench the reaction with water. Extract the resulting mixture with EtOAc; combine the extract(s); dry the extracts with magnesium sulfate; filter; and concentrate the filtrate under reduce pressure to provide a residue. Purify the title compound using silica gel chromatography eluting with a gradient of EtOAc in hexanes (0-100%). Further purify the title compound using a second silica gel chromatography eluting with a gradient of 0-10% MeOH in DCM. Concentrate the appropriate fractions under reduced pressure to provide the title compound as a glassy yellow solid (90 mg, 44.6%). MS (m/z): 435 (M+1).

EXAMPLE 2

[4-[6-(Aminomethyl)-2-methyl-pyrimidin-4-yl]oxyphenyl]methanesulfonamide

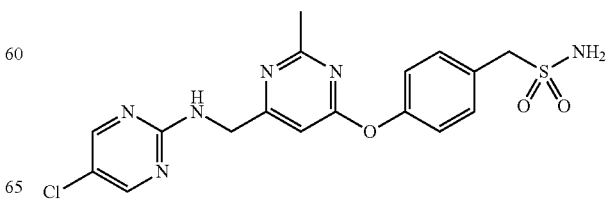

The compound of Example 2 can be made by the method as set forth below.

Preparation 8

(4-Hydroxyphenyl) methanesulfonamide

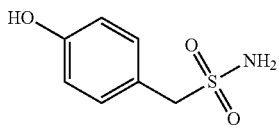 [SMILES: NS(=O)(=O)Cc1ccc(O)cc1]

Preparation 8 is prepared essentially by Preparation 1, Method A. MS (m/z): 205 (M+H$_2$O).

Preparation 9

Ethyl 2-methyl-6-oxo-1H-pyrimidine-4-carboxylate

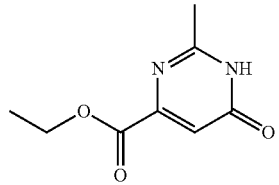

Add acetamide hydrochloride salt (13.9 g, 147 mmol) to a solution of diethyl but-2-ynedioate (25 g, 147 mmol) in acetonitrile (100 mL); then slowly, dropwise add triethylamine (22.5 mL, 162 mmol) to the mixture. Heat the mixture to 80° C. and stir for 12 hours. Cool the mixture to ambient temperature and dilute it with MeOH (50 mL). Purify the title compound using silica gel chromatography eluting with a gradient of MeOH in DCM (0-10%). Combine the appropriate fractions and remove the solvents under reduced pressure to provide the title compound as a brown solid (7.4 g, 27.5%). MS (m/z): 183 (M+1).

Preparation 10

2-Methyl-6-oxo-1H-pyrimidine-4-carboxamide

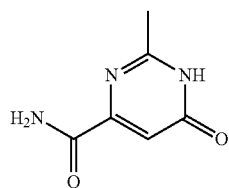

Dissolve ethyl 2-methyl-6-oxo-1H-pyrimidine-4-carboxylate (7.26 g, 39.9 mmol) in a solution of ammonia in MeOH (70 mL, 7 N) and stir the mixture for 17 hours at ambient temperature. Remove the solvents under reduced pressure to provide the title compound as a black solid (5.7 g, 93.4%). MS (m/z): 154 (M+1).

Preparation 11

6-Chloro-2-methyl-pyrimidine-4-carbonitrile

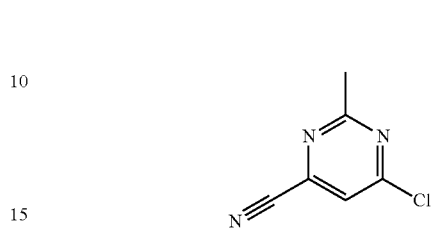

Combine 2-methyl-6-oxo-1H-pyrimidine-4-carboxamide (46 g, 140 mmol) with phosphoryl chloride (32.5 mL, 349 mmol); heat the mixture to 100° C.; and stir for 17 hrs. Remove excess phosphoryl chloride under reduced pressure to provide a black slurry. Slowly add the slurry to water (700 mL) and filter the mixture through CELITE®. Extract the filtrate with Et$_2$O. Combine the extracts; dry the over magnesium sulfate; remove the volatile solvents from the filtrate under reduced pressure to provide a black solid. Purify the title compound using silica gel flash column chromatography eluting with a gradient of MeOH/DCM (0-10%). Combine the appropriate fractions and remove the solvents under reduced pressure to provide the title compound as a yellow solid (2.5 g, 12%). MS (m/z): 154 (M+1).

Preparation 12

[4-(6-Cyano-2-methyl-pyrimidin-4-yl)oxyphenyl] methanesulfonamide

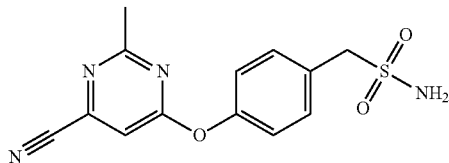 [SMILES: Cc1nc(C#N)cc(Oc2ccc(CS(N)(=O)=O)cc2)n1]

Dissolve 6-chloro-2-methylpyrimidine-4-carbonitrile (628 mg, 4.1 mmol) in DMF (15 mL) at RT under a nitrogen atmosphere. Add (4-hydroxyphenyl)methanesulfonamide (859 mg, 4.1 mmol) and potassium carbonate (1.13 g, 8.2 mmol) to the solution. Stir at ambient temperature for 3 hours. Pour the mixture into a brine solution, and extract with EtOAc. Combine the extracts; dry over magnesium sulfate; filter; and concentrate the filtrate under reduced pressure to provide the title compound (80% pure, 1.5 g, 96.4%). MS (m/z): 305 (M+1).

Alternative Preparation 12

Combine (4-hydroxyphenyl)methanesulfonamide (55 g, 269.1 mmol) and 6-chloro-2-methylpyrimidine-4-carbonitrile (45.5 g, 296 mmol) in acetonitrile (605 mL) at 22° C. Place the mixture in ultrasound bath for 5 min and stir at 22° C. for 10 min. Add potassium carbonate (325 mesh) (75.9 g, 538.2 mmol) to the solution and stir at 22° C. for 4 hours. Filter the mixture and rinse the solid with acetonitrile (3×150 mL). Concentrate the filtrates to give a brown solid. Slurry the solid in methyl-tert-butyl ether (200 mL) and collect the solid. Rinse the solid with methyl tert-butyl ether and water (2×200 mL). Collect the solid and dry the wet solid in a vacuum oven, 15 mbar, 45° C. to provide the title compound as solid, 67.21 g, 79% yield, MS (m/z): 305 (M+1).

Preparation 13

[4-[6-(Aminomethyl)-2-methyl-pyrimidin-4-yl]ox-yphenyl]methanesulfonamide

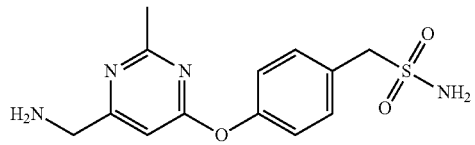 [SMILES: Cc1nc(CN)cc(Oc2ccc(CS(N)(=O)=O)cc2)n1]

Preparation 13 is prepared essentially by the method of Preparation 7 (or 4). MS (m/z): 309 (M+1).

Combine triethylamine (117.83 mL) and palladium 10% on charcoal (20.10 g) to a solution of [4-(6-cyano-2-methyl-pyrimidin-4-yl)oxyphenyl]methanesulfonamide (67 g, 211.35 mmoles) in a mixture of 1,4-dioxane (469 mL) and EtOH (201 mL; 159.05 g) in a PARR reactor. Maintain the mixture at 22° C. Seal the reactor and pressurize it with hydrogen (400 PSI). Shake the reactor for 18 h while maintaining it at 22° C. Thereafter open the reactor and filter of the solids. Rinse the solid residue with MeOH (1 L), a mixture of dioxane/MeOH 1:1 (1 L), and MeOH (3×1 L). Collect and concentrate the filtrate to provide a solid, Collect and dry the solid in a vacuum oven, (45° C., 15 mbar) to provide the title compound as yellow solid, 62.41 g, 77% yield. MS (m/z): 309 (M+1).

EXAMPLE 2

[4-[6-(Aminomethyl)-2-methyl-pyrimidin-4-yl]ox-yphenyl]methanesulfonamide

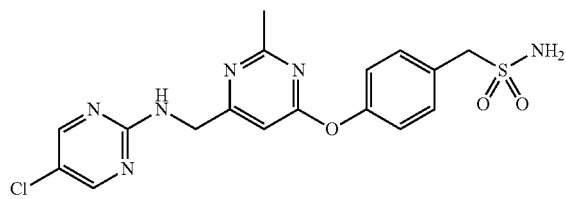 [SMILES: Cc1nc(CNc2ncc(Cl)cn2)cc(Oc2ccc(CS(N)(=O)=O)cc2)n1]

Example 2 is prepared essentially by final step in Method A for Example 1 above. MS (m/z): 421 (M+1).

ALTERNATIVE PREPARATION FOR EXAMPLE 2

Add 2,5-dichloropyrimidine (24.76 g, 162.9 mmoles) to a solution of [4-[6-(Aminomethyl)-2-methyl-pyrimidin-4-yl] oxyphenyl]methanesulfonamide (62 g, 162.9 mmoles; 62.00 g) in dimethyl sulfoxide (620 mL) at 22° C. Stir the mixture for 5 min and add potassium fluoride (10.51 g, 179.1 mmoles). Heat the mixture to 120° C. for 2 h; then cool it to 22° C. Pour the mixture into water-ice (1.2 L) and filter the suspension. Collect the solid and slurry it in water (100 mL) then collect the solid. Purify this solid via flash chromatography (1500 g column; eluent: DCM/MeOH 100:0 to 95:5; 1 L fractions, charge in DCM/MeOH 80:20 (500 mL). Collect the appropriate fractions and concentrate to provide a solid. Slurry the solid in isopropyl alcohol (250 mL), place the resulting suspension in an ultrasound bath for 5 min Collect the solid and rinse it with isopropyl alcohol to provide a pale yellow solid. Again suspend solid in isopropyl alcohol (600 mL) and place the suspension in ultrasound bath for 5 min Concentrate the alcohol suspension via a rotavap at 80° C. Collect and dry the solid under a vacuum (0.5 mbar, 22° C.) for 1 h. Add the solid to EtOH (600 mL) and place the mixture in ultrasound bath for 5 min Concentrate the mixture via a rotavap at 60° C. Collect and dry the yellow solid under vacuum 0.5 mbar, 22° C. for 1 h.

Suspend the solid in EtOH (680.2 mL). Warm the resulting suspension to 95° C. and add dimethyl sulfoxide (331.1 mL) to provide a clear yellow solution. Remove water with the EtOH (680 mL) by distilling the solvent using a dean-stark/reflux condenser under a nitrogen atmosphere. Additional EtOH (680 mL) may be added to azeotrope off remaining water. Thereafter add water (421.8 mL) and stir the mixture for 30 min at 95° C. Cool the mixture to 22° C. and stir it for 18 h. Filter the suspension. Collect and rinse the solid with water (2×100 mL). Dry the solid under vacuum (10 mbar, 40° C., 18 h) to provide the title compound as a yellow solid, 41.3 g, 61% yield, MS (m/z): 421 (M+1).

General Biology

Atherosclerotic vascular disease remains one of the leading causes of mortality and morbidity in industrial societies. One of the well-understood risk factors for that disease is a high concentration of Low Density Lipoprotein (LDL) cholesterol in circulation. Despite the availability of multiple classes of therapeutic agents that lower LDL cholesterol, including the leading therapeutic class, statins, the incidence of major cardiovascular events remains high in the patients with Coronary Heart Disease (CHD). In addition, there is a subset of patients that are intolerant to the most effective therapy, statins (Gotto, A. M., and Moon, J. E., Nature Rev. Cardiol., (2013) 10:560-570). Compounds from that class lower LDL cholesterol, chiefly by up regulation of the LDL receptor and subsequent re-uptake of LDL into the liver. An alternative, and potentially equally effective method, would be lowering of the secretion of Very Low Density Lipoproteins (VLDL), which eventually are converted into LDL in circulation. Two new classes of therapeutic agents, inhibitor of Microsomal Triglyceride Transfer Protein (MTP), lomitapide, and inhibitor of synthesis of ApoB, mipomersen, both of which reduce secretion of VLDL, were shown to reduce LDL cholesterol. However, each of those agents is associated with adverse events, which limits their utility. In particular, therapy with lomitapide is associated with 8-fold increase in the liver fat content. In contrast, inhibition of DGAT2 will reduce production of triglycerides in the liver, which in turn will lead to reduction of VLDL secretion and subsequent lowering of LDL cholesterol. Moreover, scientific statement from the American Heart Association supports therapeutic targeting of elevated triglycerides as means to reduce residual cardiovascular risk (Miller, M. et al, Circulation (2011) 123: 2292-2333 Inhibition of DGAT2 will lower circulating triglycerides and thus provide additional protection from cardiovascular events.

Diacylglycerol Acyltransferase 2 (DGAT2) Biochemical Assay

The in vitro inhibitory activity of compounds against human DGAT2 is evaluated in this assay. The assay uses recombinant human DGAT2 with a FLAG tag at the amino terminus, expressed in genetically engineered insect SF9 cells, and purified through affinity chromatography.

DGAT2 catalyzes transfer of an acyl moiety from acyl-Coenzyme A onto diacylglycerol, to form triacylglycerol. In this particular embodiment of the assay oleate is used as the acyl moiety that is transferred. To facilitate miscibility of all lipid components, all lipids used in the assay contain oleyl moiety as the only acyl group.

Prior to starting the assay prepare a mixture of dioleoyl glycerol (DOG) and dioleoyl phosphatidylcholine (DOPC) at 3:7 molar ratio. Mix appropriate amount of DOPC and DOG dissolved in chloroform in a borosilicate glass test tube. Evaporate the solvent under stream of argon to form a film of lipid. Subsequently, place the test-tube under vacuum (<1 Torr) for 2 hrs to remove residual solvent. Add appropriate amount of buffer containing TrisHCl (pH 7.5, 150 mM), and sucrose (250 mM) to achieve 20 mM concentration of total lipid. Assure complete suspension of the lipid film by vigorous vortexing. Sonicate the contents of the tube in a water bath sonicator under standing wave conditions until the suspension turns from turbid to translucent, to assure conversion of liposomes into small unilamellar vesicles (SUVs)

Prepare the test compound by dissolving it and serially diluting in half-log increments in DMSO. For each concentration, perform 10-fold step dilution of compound solution in DMSO into buffer containing TrisHCl (pH 7.5, 150 mM), and sucrose (250 mM).

Mix SUV suspensions and compound solution with other components of the assay to achieve the following concentration of individual ingredients: TrisHCl (pH 7.5, 150 mM), sucrose (250 mM), $MgCl_2$ (5 mM), dithiothreitol (DTT) (0.5 mM), oleoyl coenzyme A (oleoyl-CoA) (12 µM), 1-$^{14}$C oleoyl coenzyme A (oleyl-CoA-$^{14}$C) (8 µM), dioleoyl glycerol (DOG) (0.6 mM), and dioleoyl phosphatidylcholine (DOPC) (1.4 mM), DGAT2 protein (0.5 nM), DMSO (1%, v/v), with test compound concentration within a 1 nM to 100 µM range, in 30 µl total volume. Incubate the reaction for 1 hr at RT (approximately 21° C.) in individual wells of a 384-well plate. After 1 hr, stop the reaction by adding 23 µl stop solution containing a mixture of Isopropanol:EtOH:Heptane: DI water: 1 N NaOH (59:12.5:15:11:2.5, by volume). Add 42 µL Microscint E and then incubate mixture overnight to extract the triglyceride into the organic solvent layer containing scintillant. Measure the radioactivity using a Perkin-Elmer TopCount instrument. Establish a background measurement for the reaction by repeating the above procedure, but without including enzyme or the test compound in the reaction mixture. Calculate the degree of inhibition of DGAT2 by measuring the radioactivity at 10 different concentrations for each compound. Determine the $IC_{50}$ for each compound using 4 parameter logistic curve fit. The geometric mean for the calculated $IC_{50}$ values for Examples 1 and 2 are listed in Table 1. The data listed in Table 1 demonstrate that both Examples 1 and 2 inhibit human DGAT2 in an in vitro buffer assay.

TABLE 1

| Example | $IC_{50}$ (µM)<br>n = number of experiments |
|---|---|
| 1 | 0.091 (n = 19, sd = 0.066) |
| 2 | 0.12 (n = 13, sd = 0.076) | n = number of experiments
sd = standard deviation

Diacylglycerol Acyltransferase 2 (DGAT2) Cell-Based Assay

The inhibitory activity of compounds against human DGAT2 in a cell environment is evaluated in this assay. This assay uses human hepatoma cell-line, HepG2, as a source of acyltransferase activity.

HepG2 cell line is a commonly used model for metabolic reactions that occur in human hepatocytes in vivo. Synthesis of triglyceride in this cell line is followed by measuring incorporation of isotopically labeled oleate into triolein (a triglyceride with 3 oleoyl moieties).

Dispense the HepG2 cells into a 96-well microplate, which has been previously coated with Poly-D-lysine, in an amount of 50,000 cells/well in 100 µL Minimal Essential Media (MEM) with 10% Fetal Bovine Serum (FBS). Incubate the cells for 16 hr at 37° C. Replace the cell culture medium with MEM containing 2% Bovine Serum Albumin Dissolve the test compound in 0.5% DMSO and prepare serial dilutions in half-log increments. Add the serially diluted test compound into separate wells. Incubate for 0.5 hr at 37° C. Thereafter replace the cell culture medium with a medium of the same composition, but which includes 50 µM $^{13}C_{18}$-oleate and 300 µM hydropropyl-β-cyclodextrine. Incubate for an additional 4 hr at 37° C. Discard the cell culture medium by flipping the microplate over thereby draining the wells and then soaking up any residual media from the wells with a paper towel. Dry the microplate at ambient temperature (~21° C.) for 10 min. Add aliquots of 125 µL of solvent (isopropyl alcohol:tetrahydrofuran:methanol:chloroform, in a ratio of 90:10:2.5:2.5 v/v), an internal standard for phosphatidylcholine (PC), and an internal standard for triacylglycerol (TG) to each well. Seal and shake the plate for 30 min at ambient temperature. Transfer 100 µL aliquots of the upper phase of each well into a wells of a deep-well plate (2 mL per well). Analyze the contents of the wells using mass-spectrometry analysis. Measure both triolein with a single $^{13}C_{18}$-oleate moiety and POPC using liquid chromatography/mass spectroscopy method (LC/MS). The degree of incorporation of a single $^{13}C_{18}$-oleate moiety into triolein, normalized to the concentration of 1-palmitoyl-2-oleoyl-phosphatidylcholine (POPC) is used as a measure of DGAT2 activity.

Determine the $IC_{50}$ for each compound, using a 4 parameter logistic curve fit. The geometric mean for the calculated $IC_{50}$ values for Examples 1 and 2 are listed in Table 2 below. The data listed in Table 2 demonstrate that both Examples 1 and 2 inhibit human DGAT2 in a cell based assay.

TABLE 2

| Example | $IC_{50}$ (µM) |
|---|---|
| 1 | 0.15 (n = 2) |
| 2 | 0.15 (n = 3) | n = number of experiments

In Vivo Pharmacodynamic Assay

This assay measures the potency of compounds by measuring the reduction in plasma triglycerides in mice treated with the test compounds compared to control animals that are treated only with the vehicle solution. Male, C57BL6 mice (10-11 weeks old, each approximately 22 g in weight) are used in this assay.

Triglycerides synthesized in the liver are secreted into circulation as a component of the Very Low Density Lipoprotein (VLDL). To prevent degradation of triglycerides in circulation by the Lipoprotein Lipase (LPL), this assay uses IV injection of a detergent, tyloxapol, which inhibits activity of LPL. Since another enzyme, DGAT1, participates in the synthesis of liver triglyceride, a saturating dose of a DGAT1 inhibitor (sodium {trans-4-[4-(4-amino-7,7-dimethyl-7H-pyrimido[4,5-b][1,4]oxazin-6-yl)phenyl]cyclohexyl}acetate, IUPAC ACDLABS naming convention, see Dow et al. *Bioorg. & Med. Chem.*, (2011) 21(20), 6122-6128) is also used in this assay.

Prepare a suspension of the test compound (DGAT2 inhibitor) mixed with the DGAT1 inhibitor in a suitable vehicle, to assure dosing of 10 mL/kg compound suspension and 3 mg/kg dose of the DGAT1 inhibitor. In this set of experiments the vehicle is 1% Hydroxyethylcellulose, 0.25% Polysorbate 80, and 0.05% Antifoam in purified water. Fast the mice for 4 hours prior to treatment. Administer to the test mice, by gavage, the suspension of the test compound (DGAT2 inhibitor) at 5 doses ranging from 0.1 to 10 mg/kg, together with the 3 mg/kg dose of the DGAT1 inhibitor. Similarly administer to a set of control mice the vehicle alone (10 mL/g). Thirty minutes later, administer to each mouse, by retro-orbital injection, a 400 mg/kg dose of tyloxapol. After an additional 30 minutes, euthanize the mice with $CO_2$.

Collect the blood via cardiac puncture into tube containing the anti-coagulant EDTA. Collect the plasma following centrifugation of blood at 3,000 g for 10 min. Freeze the plasma samples on dry ice until they are to be analyzed. Thaw the samples using wet ice. Determine the concentration of triglycerides in the plasma using an automated clinical chemistry analyzer. Reduction in total triglycerides in the test mice is calculated relative to the concentration of triglycerides in the control mice. The results for Examples 1 and 2 are listed below in Table 3. The data in Table 3 demonstrates that Examples 1 and 2 reduce the concentration of plasma triglycerides.

TABLE 3

| Example | $ED_{50}$ (mg/kg) |
|---------|-------------------|
| 1       | 0.29              |
| 2       | 0.27              |

In Vivo Efficacy Model

This assay measures the potency of compounds by measuring the reduction in low density lipoprotein cholesterol (LDL-c), very low density lipoprotein cholesterol (VLDL-c), and triglycerides (TG). Male, LDL receptor-deficient mice (29 weeks old, each approximately 30 g in weight) are used in this assay.

LDL receptor deficient mice are selected for that assay to demonstrate that any measured reduction of LDL cholesterol is achieved independently of the LDL-receptor mediated uptake of LDL into the liver.

Feed the mice a standard mouse chow diet for two weeks prior to dosing. Prepare a test solution for oral gavage by suspend the compounds in acacia at 0.3, 1, and 3 mg/mL. Separate the mice into a test group and a control group. Thereafter at the first day of the third week dose the mice in the test group with the test solution for fourteen days, BID. Similarly dose the mice in the control group with just the vehicle without any of the test compound. Four hours after the last dose euthanized the mice with $CO_2$. Immediately collect the blood via cardiac puncture. Isolate the serum to measure serum triglycerides as well as cholesterol in individual lipoprotein fractions. Separate the lipoprotein fractions by known HPLC methods. Determine the cholesterol concentration associated with each lipoprotein fraction by a colorimetric method (Roche Cholesterol/HP Reagent 11875540), using isolated lipoprotein fractions with known cholesterol concentration as standards. Results obtained at the highest dose, 30 mg/kg, BID, expressed as the percentage of change in comparison of the LDL-c, VLDL-c and TG serum concentrations of mice in the test group to those of mice n the control group. The results for Example 1 are listed in Table 4. The results demonstrate that Example 1 reduces LDL-c, VLDL-c and TG serum concentrations.

TABLE 4

| Parameter     | % change |
|---------------|----------|
| LDL-c         | −51%     |
| VLDL-c        | −75%     |
| Triglycerides | −63%     |

The results listed in Table 5 demonstrate that Example 2 also reduces LDL-c, VLDL-c and TG serum concentrations. To enable absorption of Example 2 at the 30 mg/kg dose, prepare that compound as 1:1 (w/w) dry mixture with hydroxypropyl methylcellulose prior to addition to acacia vehicle.

TABLE 5

| Parameter     | % change |
|---------------|----------|
| LDL-c         | −55%     |
| VLDL-c        | −82%     |
| Triglycerides | −72%     |

A treating physician or other medical person will be able to determine an effective amount of the compound for treatment of a person in need. Preferred pharmaceutical compositions can be formulated as a tablet or capsule for oral administration. The tablet or capsule can include a compound of the present invention in an amount effective for treating a patient in need of treatment for cardiovascular disease, dyslipidemia, atherosclerosis, or hypertriglyceridemia.

The exemplified compounds of the present invention can be used alone or combined with one or more additional therapeutic agents.

The exemplified compounds can be combined with additional therapeutic agents used to treat cardiovascular diseases such as: niacin, aspirin, statins, CETP inhibitors, and fibrates. Examples of statins include atorvastatin, cerivastatin, fluvastatin, lovastatin, mevastatin, pitavastatin, pravastatin, rosuvastatin, and simvastatin. Examples of fibrates include bezafibrate, ciprofibrate, clofibrate, gemfibrozil, and fenofibrate.

The exemplified compounds and the additional therapeutic agent(s) can be administered either together through the same delivery route and device such as a single pill, capsule or tablet; or separately administered either at the same time in separate delivery devices or sequentially.

What is claimed is:

1. A compound of the Formula:

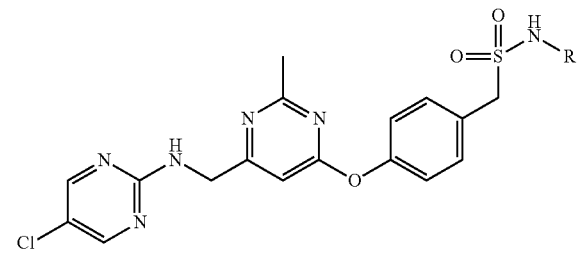

wherein R is H or —CH₃, or a pharmaceutically acceptable salt thereof.

2. A compound according to claim 1 wherein R is H, or a pharmaceutically acceptable salt thereof.

3. A compound according to claim 1 wherein R is —CH₃, or a pharmaceutically acceptable salt thereof.

4. A method of treating a patient in need of treatment for cardiovascular disease the method comprises administering to the patient an effective amount of a compound, according to claim 1, or a pharmaceutically acceptable salt thereof.

5. A method of treating a patient in need of treatment for cardiovascular disease the method comprises administering to the patient an effective amount of a compound, according to claim 2, or a pharmaceutically acceptable salt thereof.

6. A method of treating a patient in need of treatment for dyslipidemia, the method comprises administering to the patient an effective amount of a compound, according to claim 1, or a pharmaceutically acceptable salt thereof.

7. A method of treating a patient in need of treatment for dyslipidemia, the method comprises administering to the patient an effective amount of a compound, according to claim 2, or a pharmaceutically acceptable salt thereof.

8. A method of treating a patient in need of treatment for atherosclerosis, the method comprises administering to the patient an effective amount of a compound, according to claim 1, or a pharmaceutically acceptable salt thereof.

9. A method of treating a patient in need of treatment for hypertriglyceridemia, the method comprises administering to the patient an effective amount of a compound according to claim 1, or a pharmaceutically acceptable salt thereof.

10. A method of treating a patient in need of treatment for hypertriglyceridemia, the method comprises administering to the patient an effective amount of a compound according to claim 2, or a pharmaceutically acceptable salt thereof.

11. A pharmaceutical composition comprising a compound according to claim 1, or a pharmaceutically acceptable salt thereof, and at least one of a pharmaceutically acceptable carrier or excipient.

12. A pharmaceutical composition comprising a compound according to claim 2, or a pharmaceutically acceptable salt thereof, and at least one of a pharmaceutically acceptable carrier or excipient.

13. A method of treating a patient in need for treatment for cardiovascular disease, dyslipidemia, atherosclerosis, or hypertriglyceridemia wherein the method comprises administering to the patient an effective amount of a pharmaceutical composition according to claim 12.

14. A process for the preparation of a compound of the Formula:

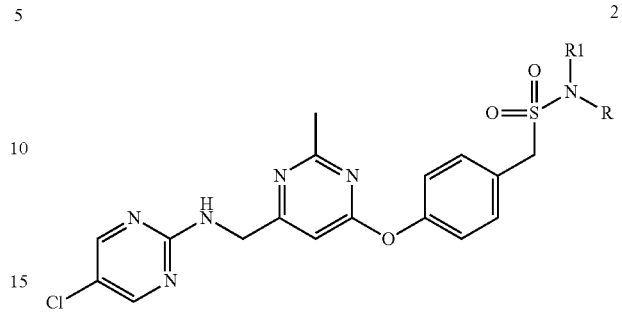

wherein R is H or —CH₃, and
R1 is H or a nitrogen protecting group, said method comprising:
reacting a compound of Formula 3

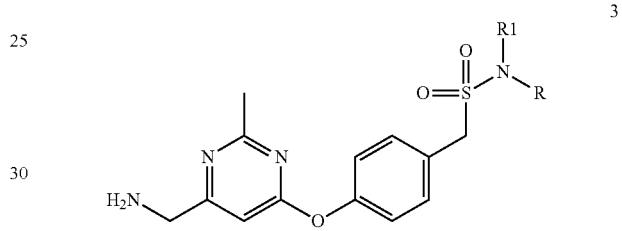

with a compound of Formula 4 below:

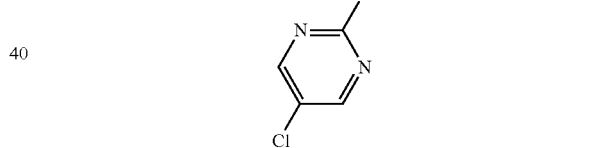

15. The process of claim 14 wherein where R1 is a protecting group and the process further comprises removing the protecting group.

* * * * *